United States Patent [19]

Markussen

[11] Patent Number: 5,317,092
[45] Date of Patent: May 31, 1994

[54] PROTEIN PURIFICATION METHOD
[75] Inventor: Jan Markussen, Herlev, Denmark
[73] Assignee: Novo Nordisk A/S, Novo Alle, Denmark
[21] Appl. No.: 721,582
[22] PCT Filed: Nov. 20, 1990
[86] PCT No.: PCT/DK90/00298
  § 371 Date: Jun. 5, 1992
  § 102(e) Date: Jun. 5, 1992
[87] PCT Pub. No.: WO91/07428
  PCT Pub. Date: May 30, 1991
[30] Foreign Application Priority Data
  Nov. 20, 1989 [DK] Denmark .................... 5807/89
[51] Int. Cl.$^5$ .................... C07K 3/20; C07K 15/28
[52] U.S. Cl. .................... 530/413; 530/345; 530/351; 530/381; 530/383; 530/399; 530/412; 435/7.2
[58] Field of Search ........... 530/413, 351, 345, 381, 530/383, 399, 412; 435/7.2

[56] References Cited

U.S. PATENT DOCUMENTS

| | | | |
|---|---|---|---|
| 4,123,427 | 10/1978 | Daniel | 530/413 |
| 4,499,014 | 2/1985 | Estis | 530/413 |
| 4,518,526 | 5/1985 | Olson | 435/68 |
| 4,568,488 | 2/1986 | Lee-Huang et al. | 530/413 |
| 4,677,196 | 6/1987 | Rausch et al. | 530/412 |
| 4,705,848 | 11/1987 | Yang et al. | 530/399 |
| 4,762,706 | 8/1988 | McCormick et al. | 435/68 |
| 4,845,032 | 7/1989 | Obermeier | 435/68 |
| 4,965,344 | 10/1990 | Hermann | 530/412 |
| 4,977,248 | 12/1990 | Creighton | 530/412 |
| 5,136,027 | 8/1992 | Pope | 530/404 |

FOREIGN PATENT DOCUMENTS

| | | |
|---|---|---|
| 0127737 | 12/1984 | European Pat. Off. . |
| 0199568 | 10/1986 | European Pat. Off. . |
| 0234545 | 9/1987 | European Pat. Off. . |
| 0249932 | 12/1987 | European Pat. Off. . |
| WO88/08849 | 11/1988 | PCT Int'l Appl. . |
| WO88/08850 | 11/1988 | PCT Int'l Appl. . |
| 2093039 | 8/1982 | United Kingdom . |
| 2173803 | 10/1986 | United Kingdom . |
| 8501941 | 5/1985 | World Int. Prop. O. . |
| 8600910 | 2/1986 | World Int. Prop. O. . |
| 8604336 | 7/1986 | World Int. Prop. O. . |

OTHER PUBLICATIONS

Monaco et al., The EMBO Journal, vol. 6, No. 11, pp. 3253-3260 (1986).

*Primary Examiner*—Michael G. Wityshyn
*Assistant Examiner*—C. Sayala
*Attorney, Agent, or Firm*—Steve T. Zelson; Karen A. Lowney

[57] ABSTRACT

In a method of recovering proteins, an antibody raised against a peptide comprising at least a fragment of the protein is immobilized on a solid support, a crude preparation of the protein is contacted with the antibody under conditions resulting in a partial, reversible unfolding of the protein to obtain binding of the protein to the antibody, and the protein is eluted from the solid support under non-denaturing conditions to recover the protein in a form in which it is refolded into its native conformation.

19 Claims, No Drawings

PROTEIN PURIFICATION METHOD

FIELD OF INVENTION

The present invention relates to an immunoaffinity chromatographic method of recovering proteins or polypeptides in substantially pure form.

BACKGROUND OF THE INVENTION

In the production of proteins or polypeptides from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides in the crude material containing this protein.

One widely practiced method of ensuring such a separation is affinity chromatography which generally involves a specific interaction between an insoluble immobilized ligand and a soluble protein, cf. A. Johnstone and R. Thorpe, *Immunochemistry in Practice*, 2nd Ed., Blackwell Scientific Publications, 1987, pp. 207-240. By interacting with the ligand, the protein is temporarily rendered insoluble and is retained on the solid support on which the ligand is immobilized while the soluble contaminants are eluted. The binding of the protein to the ligand conventionally takes place in an aqueous buffer at a neutral pH. The protein is subsequently released from the immobilized ligand by a change in the elution conditions, such as a jump in the pH, an increase in temperature or elution with a denaturing agent, an organic solvent or an unphysiologically high concentration of a salt. As a result of these procedures, the protein is often recovered in denatured form and will have to be subjected to further procedures in order to become available in its native conformation.

Examples of commonly used ligands are antibodies, in particular monoclonal antibodies, which can be made to be more selective and to bind more firmly most other known ligand and which are therefore preferred as they result in a higher purity of the eluted protein product. In order to obtain an antibody in sufficient quantities, however, the protein to be purified should usually be available in substantially pure form for the immunization procedure. This approach to solve the problem therefore implies that the problem of protein recovery has already been solved by other means.

The amino acid sequence, i.e. primary structure, of many proteins may initially be arrived at by deduction from the DNA sequence of their corresponding genes. This procedure often takes place before the protein product itself has been isolated. Knowledge of the amino acid sequence of a protein makes it possible to synthesize peptide fragments thereof, e.g. by solid phase peptide synthesis techniques. Such peptide fragments may then be used to raise antibodies against the protein to be purified. However, it has often been found that the thus generated antibodies are reactive with the synthetic peptide fragment against which they have been raised, but not with the native protein of which the peptide constitutes a fragment. This phenomenon is thought to be ascribable to sterical hindrance or to differences in conformation between the synthetic peptide and the native protein, the peptide fragment having a highly flexible conformation in which side chains are exposed, whereas the same fragment is less flexible in the entire protein and has a number of its side chains, in particular hydrophobic side chains, embedded in the interior of the protein. Whether or not this is the correct explanation, it is at any rate often the case that antibodies raised against synthetic peptide fragments of a native protein do not bind the entire native protein. Similar results are also often obtained when denatured proteins are used as immunogens.

SUMMARY OF THE INVENTION

It has now surprisingly been found that antibodies against synthetic peptide fragments or denatured proteins may be useful for the isolation of their corresponding native proteins if the conditions of adsorption to and desorption from the immobilized ligand are reversed.

Accordingly, the present invention relates to a method of recovering a protein or polypeptide of interest, the method comprising (a) immobilizing, on a solid support, an antibody raised against a peptide which comprises at least a fragment of said protein or polypeptide, (b) contacting a crude preparation of the protein or polypeptide of interest with the immobilized antibody under conditions resulting in a partial, reversible unfolding of the protein or polypeptide, so as to expose an amino acid sequence therein corresponding to the sequence used for raising the immobilized antibody and thereby obtain binding of the protein or polypeptide to the antibody, and (c) eluting the protein or polypeptide from the solid support under non-denaturing conditions to recover said protein or polypeptide in a form in which it is refolded into its native conformation.

DETAILED DISCLOSURE OF THE INVENTION

In the method of the invention, the crude preparation of the protein or polypeptide, which will usually be either a culture medium from which cells have been removed (for secreted proteins) or a cell lysate from which cell debris has been removed (for intracellular proteins), may be contacted with the solid support in a solvent, such as an aqueous buffer, before or after imposing the conditions resulting in partial unfolding of the protein or polypeptide. In most cases, however, it will be most convenient to impose said conditions before contacting the preparation with the immobilized antibody. In this way, the structure of the protein or polypeptide will be loosened to such an extent that the immunogenic determinants thereon against which the immobilized antibody has been raised will be sufficiently exposed and therefore recognized by the antibody even when these determinants are located on the full-length protein. On the other hand, the conditions for unfolding the protein or polypeptide should not be so extreme as to result in denaturation of the antibody, thereby impairing the ability of the antibody to bind the protein or polypeptide.

Conditions resulting in a partial reversible unfolding of the protein or polypeptide may be any one of those known in the art to cause protein denaturation. Examples of such conditions comprise an increase in temperature, a substantial increase or decrease in the pH of the protein or polypeptide preparation relative to the pH of the native environment in which the protein or polypeptide is functional, the addition of a protein denaturing agent to the protein or polypeptide preparation, the addition of an organic solvent to the protein or polypeptide preparation, or an unphysiologically high concentration of a salt in the protein or polypeptide preparation, or a combination of two or more of these measures. The increase in temperature may conveniently be an increase to at least 32° C., such as an increase to between about 37° and about 60° C. The increase in the pH of the preparation may suitably be an increase to a pH of more than about 8. The pH increase may be provided by adding a suitable organic or inorganic base to the preparation, e.g. Tris, ammonia, sodium hydroxide or sodium carbonate. The decrease in the pH of the preparation may suitably be a decrease to a pH of less than about 6. The pH decrease may be provided by adding an appropriate organic or inorganic acid to the preparation, e.g. acetic acid, hydrochloric acid, sulphuric acid or phosphoric acid.

Examples of protein denaturing agents which may be useful in the method of the invention are urea, thiourea, guanidinium hydrochloride, a chaotropic agent such as a thiocyanate salt, e.g. KSCN or $NH_4SCN$, or a detergent such as sodium dodecyl sulfate, sodium deoxycholate, a polyoxyethylene alcohol (e.g. the Brij series), an octoxynol (e.g. the Triton series), Tween 20, or a glycolipid such as decanoyl methylglucoside. When the protein denaturing agent is a detergent, it may conveniently be added in an amount of 0.01-10%, preferably 0.01-1% by volume of the protein or polypeptide preparation. When the protein denaturing agent is other than a detergent, it may be added to a concentration of 0.5-6M, preferably 1-3M.

Examples of suitable organic solvents are methanol, ethanol, propanol, 2-propanol, dimethyl formamide, acetonitrile, polyethylene glycol, glycol, glycerol, phenol or 1,4-butane diol. The organic solvent may be added in an amount of up to 95 % by volume dependent on the type of solvent, alcohols (e.g. 1,4-butane diol) being the milder solvents permitting the highest solvent concentration.

When a salt is added to the protein or polypeptide preparation, it may suitably be added to a concentration of 0.5-6M, preferably 1-3M. Examples of salts which are useful for the present purpose are NaCl, $MgCl_2$ and $(NH_4)_2SO_4$, NaOAc, $K_2SO_4$, KOAc, sodium phosphates or sodium citrates.

The antibody used in step (a) of the present process may be any antibody which is capable of binding the protein or polypeptide of interest under the aforementioned conditions. Thus, the antibody may be one raised against the protein or polypeptide in denatured form or a fragment thereof comprising at least one antigenic determinant of the protein or polypeptide in question, or against a synthetic peptide with an amino acid sequence corresponding to a partial amino acid sequence of the protein or polypeptide. The partial sequence should comprise at least six amino acids in order to provide an antigenic determinant. The synthetic peptide may be prepared according to established standard methods in the field of peptide synthesis, e.g. as described in Stewart and Young, *Solid Phase Synthesis*, 2nd. Ed., Pierce Chemical Company, Rockford, Ill., USA.

The antibody employed in the method of the invention may be a polyclonal antibody. Polyclonal antibodies may be prepared by immunizing suitable animals (such as rabbits, goats, horses, sheep, mice, chickens, rats and guinea pigs) with the peptide in question and isolating the antibody from the serum in a manner known per se (cf. A. Johnstone and R. Thorpe, op cit., pp. 30-34 and 48-55). It is, however, usually preferred to employ monoclonal antibodies as these have become easy to produce in large quantities and in a high degree of purity. Furthermore., they exhibit great uniformity. Alternatively, it is possible to use a fragment of a monoclonal antibody, e.g. a Fab' or F(ab')$_2$ fragment. Monoclonal antibodies may be prepared by fusing cells producing the antibody with myeloma cells of an established cell line, selecting and cloning the resulting hybridoma cells and growing them in a suitable medium to produce the antibody and isolating the antibody from the culture, e.g. as described in A. Johnstone and R. Thorpe, op. cit., pp. 35-43.

The solid support on which the antibody is immobilized may comprise any support material conventionally employed for chromatographic procedures. Thus, the solid support may typically comprise a polymer, such as a resin, e.g. an acrylic resin, a silica-based or a polymer based on a polysaccharide such as agarose, dextran or cellulose which is optionally modified by functional moieties provided for the purpose of facilitating covalent bonding of the antibody to the support. Examples of useful functional moieties are amino, cyano, thio, epoxy, imido, hydroxyl, keto, carboxyl, amido, ester or acyl groups, or groups containing a halide, or ethylene sulfones such as vinyl sulfone. The support may suitably be in the form of beads or particles which may be packed in columns in a manner known per se in the field of chromatography, or the support may be used in a batch process.

The protein or polypeptide to be isolated by the method of the invention may be any protein or polypeptide which may advantageously be prepared in the present way, in particular proteins or polypeptides which have been found difficult to purify satisfactorily by any of the conventional purification procedures. In the present context, the term "polypeptide" is distinguished from the term "protein" by indicating a fragment of a protein, a fusion of one protein with another, or a fragment thereof, or a hybrid of at least two protein fragments, whereas the term "protein" is understood to mean a full-length or native amino acid sequence or a derivative thereof. Examples of proteins or polypeptides which may suitably be prepared by the present method are growth hormone, Factor VII, Factor VIII, tissue plasminogen activator, interleukin-2, interferon, growth factors and membrane proteins such as growth factor receptors, the insulin receptor or the glucagon receptor.

Desorption of the protein or polypeptide of interest from the solid support is achieved by reversing the conditions under which the protein or polypeptide is partially unfolded, i.e. in the absence of the factor or factors responsible for the loosening of the protein structure. Desorption may typically be achieved by the addition of a neutral buffer, in particular an aqueous buffer, for instance a phosphate buffer, Tris buffer, Hepes buffer, bicarbonate buffer or borate buffer, resulting in the refolding of the protein or polypeptide into its native conformation whereby it no longer binds to the antibody and is consequently eluted. The eluted protein or polypeptide may, if desired, be concentrated by precipitation, ultrafiltration, or lyophilization in a manner known per se.

Apart from permitting the use of antibodies raised against synthetic peptides or protein fragments for the recovery of native proteins, the method of the present invention has the added advantage of resulting in the recovery of a protein product which is refolded and therefore considerably more stable than the denatured proteins resulting from conventional immunoaffinity chromatographic procedures. Furthermore, since the protein or polypeptide is eluted with a neutral buffer, no denaturing agent (or salt or organic solvent) will have to be removed from the purified protein product.

It has previously been suggested to obtain purified and biologically active proteins by denaturing and subsequently renaturing the proteins, cf., for instance, U.S. Pat. No. 4,677,196 EP 196 146, U.S. Pat. No. 4,656,255, U.S. Pat. No. 4,705,848, WO 88/08849 and WO 88/08850. These publications, however, address a different problem which is the necessity of solubilizing protein aggregates (the so-called "inclusion bodies") often produced in recombinant microorganisms in order to obtain the biologically active protein. In some cases, it is suggested to purify the protein before the denaturation/renaturation procedure (cf. WO 88/08850), and in others the renatured, solubilized protein is concentrated by dialysis rather than by chromatography (cf. U.S. Pat. No. 4,656,255). Even in those procedures where denaturation and renaturation is combined with chromatographic procedures, denaturing and renaturing does not form part of the purification procedure as such, but is merely a way of providing the protein in solubilized form. Protein purification by chromatography invariably follows the renaturation stage rather than being performed substantially simultaneously therewith as in the present method. One reason for this may be that the previously described processes do not employ any affinity chromatography which makes it unfeasible to combine procedures for obtaining a correctly folded, biologically active product with procedures for obtaining a purified product. The present method therefore represents a more convenient method of isolating proteins than the previously suggested methods of protein recovery due to the use of immobilized antibodies for the chromatography in combination with stepwise unfolding and refolding of the product to be recovered.

The present invention is further illustrated in the following example which is not be construed as in any way limiting the scope and spirit of the invention.

EXAMPLE

Synthesis of HIR-α(39–75)-NH₂

Synthesis of (SEW ID NO: 1):
H-Phe-Lys-Thr-Arg-Pro-Glu-Asp-Phe-Arg-Asp-Leu-Ser-Phe-Pro-Lys-Leu-Ile-Met-Ile-Thr-Asp-Tyr-Leu-Leu-Leu-Phe-Arg-Val-Tyr-Gly-Leu-Glu-Ser-Leu-Lys-Asp-Leu-NH₂

The fragment consisting of the amino acid residues 39–75 of the human insulin receptor α-subunit according to Ullrich et al., *Nature* 313, pp. 756–761, 1985 and Ebina et al., *Cell* 40, pp. 747–758, 1985, was synthesized as the C-terminal amide by the solid phase procedure described by Stewart and Young, *Solid Phase Synthesis*, 2nd edition, Pierce Chemical Company, Rockford, Ill., pp. 1–50.

The resin utilized was of the so-called "MBHA" type which is described in G. R. Matsueda and J. M. Stewart: PEPTIDES, 2 (1981), pp. 45–50, obtained from Applied Biosystems, U.S.A. (art No. 400229).

The following commercially available amino acid derivatives were used in the synthesis: Boc-Arg-(Tos)-OH, Boc-Phe-OH, Boc-Asp(OBzl)-OH, Boc-Ser(Bzl)-OH, Boc-Gly-OH, Boc-Ile-OH, Boc-Pro-OH, Boc-Leu-OH, Boc-Val-OH, Boc-Thr(Bzl)-OH, Boc-Glu-(OBzl)-OH, Boc-Met(O)-OH, Boc-Lys(2-Cl-Z)-OH and BocTyr(2-Br-Z)-OH.

The amino acid derivatives were coupled as symmetrical anhydrides except for Boc-Arg(Tos)-OH which was coupled as the HOBt ester.

The assembly of the peptide chain was done successively by means of an automatic peptide synthesizer (Applied Biosystems model 430A).

After the construction of the peptide chain was completed, the terminal Boc group was removed. The resin-linked peptide was washed with $CH_2Cl_2$ and dried. 800 mg of the resin-linked peptide were then subjected to cleavage and deprotection with hydrogen fluoride, using the "Low-High" procedure described by Tam et al. in J.AM.CHEM.SOC., 105, pp. 6442–55, 1983.

After the final evaporation of hydrogen fluoride the detached peptide was precipitated and washed several times with diethyl ether. The precipitated peptide was dissolved into 20 ml of 50% acetic acid and the solution was subjected to gel filtration on a column of Sephadex G-25 (registered trademark of Pharmacia, Uppsala, Sweden) and eluted with 10% acetic acid containing 15% of 2-propanol. The peptide-containing fractions were collected and the peptide was precipitated by adjustment of the pH to 7.0 using an ammonium hydroxide solution. The precipitate was isolated by centrifugation, washed several times with water and dried. Yield: 159 mg of the crude peptide.

The peptide was purified by HPLC using a column of Nucleosil TM C18 (purchased from Machery-Nagel, Düren, FRG) and as eluent a 0.1% trifluoroacetic acid in a linear gradient of acetonitrile from 40 to 60% acetonitrile over 30 min. The peptide emerged from the column at about 53% acetonitrile. The peptide was recovered from the solution by evaporation of the acetonitrile in vacuo followed by lyophilization. Yield: 30 mg of purified peptide. The amino acid analysis was in agreement with the composition of the title compound.

Preparation of Monoclonal Antibodies Against HIR-α(39–75)-NH₂

Mice were immunized every other week for 4 months with 50 μg of HIR-α(39–75)-NH₂ in Freund's adjuvant. The mice were sacrificed, and the spleen cells isolated and fused with cells of a non-immunoglobulin producing mouse myeloma cell line, as described in A. Johnstone and R. Thorpe, op. cit., pp. 37–39.

The antibody-producing hybridomas thus formed were selected and cloned by means of the limiting dilution method (cf. A. Johnstone and R. Thorpe, op. cit., pp. 39–42).

The screening for antibody-producing hybridomas was conducted using an ELISA assay procedure (cf. A. Johnstone and R. Thorpe, op. cit., pp. 257–260) in which the HIR-α(39–75)-NH₂ peptide antigen was used to coat the wells of the microtiter ELISA plate (0.1 μg per well).

A total of 14 clones was obtained. The antibodies from all 14 clones reacted with the peptide antigen and with the denatured human insulin receptor. None of the 14 antibodies reacted with the native human insulin receptor. Thus, the antibodies recognize the human insulin receptor and its α-subunit after SDS gel electrophoresis and immunoblotting, but fail to react with the native insulin receptor, e.g. as exposed on HEP G2 cells.

The clone producing the highest titer, F26, was grown in a 1 liter cell culture. The antibody was purified by adsorption to a 5×10 cm column packed with protein A Sepharose 6B (registered trademark of Pharmacia, Uppsala, Sweden) in 0.1M Tris buffer at pH 8.5, washing with the same buffer and eluting with an 0.1M citrate buffer at pH 3.0. The antibody-containing fractions were pooled, rendering 25 mg of F26 antibody in 70 ml eluent. Finally the buffer was exchanged by dialysis against PBS (phosphate buffered saline). The antibody F26 belongs to the IgG-2b class.

IMMOBILIZATION OF THE ANTIBODY F26

15 ml of protein A purified F26 antibody was dialyzed against 1 liter 0.1M NaHCO$_3$ pH 8.5 buffer for 48 h with exchange of buffer after 24 h. The dialysate was mixed with 10 ml Minileak ™ gel suspension, which is a divinyl sulfone activated, agarose-based matrix (purchased from Kem-En-Tec Biotechnology Corporation, Copenhagen, Denmark). The pH was adjusted to 8.8 and the immobilization reaction is carried out at 4° C. for 24 h using slow rotation to keep the gel in suspension. The gel was isolated by sedimentation and washed, and excessive reactive sites were blocked by the addition of 15 ml 0.1M ethanolamine, pH 8.5, keeping the gel in suspension for another 24 h at 4° C. by slow rotation. Finally, the gel was packed in a 1.5 cm diameter column, rendering a 3.5 cm bed height, and equilibrated with a 0.1M Tris buffer, pH 7.0, containing 0.1% ($^w$/v) of SDS (sodium docecylsulphate).

Reverse-mode Affinity Chromatography

The ability of the F26 antibody/Mini-leak column to bind the α-subunit of unfolded human insulin receptor, and to release it when it is refolded into its native conformation, was demonstrated using the secretable, soluble fraction of the human insulin receptor, SIR, which is the human insulin receptor from which the ectodomain as 429 amino acids have been deleted from the β-subunit, Whittaker & Okamoto, *J. Biol. Chem.* 263, 3063-3066, 1988.

The soluble fragment of the human insulin receptor (SIR) is a dimer ($\alpha_2\beta'_2$) in which the α-subunits comprise the entire sequence of the α-subunit and the β'-subunits comprise the first 194 amino acids of the β-subunit.

The SIR was purified by affinity chromatography using columns sequentially containing immobilized wheat germ agglutinin and insulin according to Yamaguchi, *J. Biol. Chem.* 258, 5045-5049, 1983. The SIR molecules were radioactively labelled with $^{125}$I using the lactoperoxidase method, Holohan et al., *Clin. Chem. Acta* 45, pp. 153-157 (1973).

The $^{125}$I-labelled SIR molecules, approximately 100 μg and about 10,000 cpm, were dissolved in 1 ml 0.1M Tris buffer, pH 7.0, containing 0.1% (w/v) of SDS. The solution was applied to the F26 antibody column, and the column was washed with 20 ml of the same buffer at a rate of 4 ml/h. Fractions of 1 ml were collected. The SIR molecules was eluted from the column by 20 ml of a 0.1M Tris buffer, pH 7.8, which was devoid of SDS, using the same rate of elution and fraction size as for absorption. The SIR containing fractions were identified by means of a gamma-counter. The result is shown in Table 1. It appears that 83% of the radiaoctiivtiy emerges with the second buffer. The volumes of the eluents correspond to about three times those of the columns.

In a control experiment a monoclonal antibody capable of binding to human insulin was immobilized as described above for the F26 antibody and tested for its ability to bind SIR molecules, using conditions identical to those described for the F26 column above. The result is shown in Table 1. Using this antibody, 97% of the $^{125}$I-labelled SIR elutes with the first, SDS-containing buffer, thus proving that the binding of SIR molecules to immobilized F26 antibody in SDS containing buffer is specific.

TABLE 1

| Immobilized antibody: | Affinity column | |
|---|---|---|
| | Anti HIR-α(39–75)-NH$_2$ | Anti human insulin |
| | % of total | |
| Radioactivity in first eluent (0.1M Tris, pH 7.0, 0.1% SDS) | 2 | 97 |
| Radioactivity in second eluent (0.1M Tris, pH 7.8) | 83 | 0 |
| Loss on column | 15 | 3 |

I claim:
1. A method of recovering a protein or polypeptide of interest, the method comprising
    (a) immobilizing, on a solid support, an antibody raised against a peptide which comprises at least a fragment comprising an antigenic determinant of said protein or polypeptide,
    (b) contacting a crude preparation of the protein or polypeptide of interest with the immobilized antibody under conditions resulting in a partial, reversible unfolding of the protein or polypeptide, so as to expose an amino acid sequence therein corresponding to the peptide used for raising the immobilized antibody and thereby obtain binding of the protein or polypeptide to the antibody, wherein the conditions resulting in a partial, reversible unfolding of the protein or polypeptide in step (b) are selected from a group consisting of an increase in temperature to between 37° and 60° C., a substantial increase or decrease in the pH of the protein or polypeptide preparation relative to the pH at which the protein or polypeptide is functional, the addition of a protein denaturing agent to the protein or polypeptide preparation, a concentration of a salt in the protein or polypeptide preparation higher than the physiological concentration of the salt, or a combination of two or more of these measures, and
    (c) eluting the protein or polypeptide from the solid support under non-denaturing conditions to recover said protein or polypeptide in a form in which it is refolded into its native conformation.
2. A method according to claim 1, wherein the pH of the preparation is higher than 8.
3. A method according to claim 1, wherein the pH of the preparation is lower than 6.
4. A method according to claim 1, wherein the protein denaturing agent is a non-detergent selected from the group consisting of urea, thiourea, guanidinium hydrochloride, or a thiocyanate salt, or a detergent.
5. A method according to claim 4, wherein the detergent is added in an amount of 0.01–10% by volume of the preparation.
6. A method according to claim 4 wherein the non-detergent protein denaturing agent is added up to a concentration of 0.5–6M.
7. A method according to claim 1, wherein the concentration of the salt in the preparation is 0.5–6M.
8. A method according to claim 7, wherein the salt is selected from the group consisting of NaCl, MgCl$_2$ and (NH$_4$)$_2$SO$_4$, NaOAc, K$_2$SO$_4$, KOAc, sodium phosphates and sodium citrates.
9. A method according to claim 1, wherein the antibody used in step (a) is raised against the protein or polypeptide of interest in denatured form or a fragment thereof comprising at least one antigenic determinant of said protein or polypeptide, or against a synthetic peptide with an amino acid sequence corresponding to a partial amino acid sequence of the protein or polypeptide of interest.
10. A method according to claim 9, wherein the antibody is a monoclonal antibody or an antigen-binding fragment thereof.
11. A method according to claim 1, wherein the support on which the antibody is immobilized in step (a) is selected from the group consisting of agarose, dextran, cellulose, silica or acrylic acid amide.
12. A method according to claim 1, wherein the protein or polypeptide of interest is selected from the group consisting of growth hormone, Factor VII, Factor VIII, tissue plasminogen activator, interleukin-2, interferon, growth factors and membrane proteins.
13. A method according to claim 1, wherein the non-denaturing conditions in step (c) comprise the use of a neutral buffer selected from the group consisting of phosphate buffers, Tris buffer, Hepes buffer, bicarbonate buffers and borate buffers.
14. A method according to claim 4, in which the thiocyanate salt is KSCN or NH$_4$SCN.
15. A method according to claim 4, in which the denaturing agent is a detergent selected from the group consisting of sodium dodecyl sulfate, sodium deoxycholate, a polyoxyethylene alcohol, an octoxynol, Tween 20, or a colipid.
16. A method according to claim 5, in which the detergent is added in a amount of 0.01–1% by volume of the preparation.
17. A method according to claim 6, in which the non-detergent denaturing agent is added to a concentration of 1–3M.
18. A method according to claim 7, in which the concentration of the salt in the preparation is 1–3M.
19. A method according to claim 12, wherein the membrane protein is selected from the group consisting of a growth factor, an insulin receptor, or a glucagon receptor.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal (v i) ORIGINAL SOURCE:
    (A) ORGANISM: synthetic (x i) SEQUENCE DESCRIPTION: SEQ ID NO: 1:

```
Phe Lys Thr Arg Pro Glu Asp Phe Arg Asp Leu Ser Phe Pro Lys Leu
1               5                   10                  15
Ile Met Ile Thr Asp Tyr Leu Leu Leu Phe Arg Val Tyr Gly Leu Glu
            20                  25                  30
Ser Leu Lys Asp Leu
            35
```